United States Patent
Dadashian et al.

(10) Patent No.: US 10,105,544 B2
(45) Date of Patent: Oct. 23, 2018

(54) IMPLANTABLE MEDICAL DEVICES INCLUDING A LASER ETCHED SURFACE IN BONDED AREAS

(71) Applicant: PACESETTER, INC., Sylmar, CA (US)

(72) Inventors: Asghar Dadashian, Porter Ranch, CA (US); Avi Bilu, Pasadena, CA (US); Ofer Rosenzweig, Chatsworth, CA (US); Sean Portune, Santa Maria, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/251,960

(22) Filed: Aug. 30, 2016

(65) Prior Publication Data
US 2018/0056077 A1    Mar. 1, 2018

(51) Int. Cl.
*A61N 1/00* (2006.01)
*A61N 1/375* (2006.01)
*A61N 1/39* (2006.01)

(52) U.S. Cl.
CPC ......... *A61N 1/3752* (2013.01); *A61N 1/3956* (2013.01)

(58) Field of Classification Search
CPC .... A61N 1/3752; A61N 1/3956; A61N 1/375; A61N 1/3787
See application file for complete search history.

(56) References Cited

U.S. PATENT DOCUMENTS

| | | | | |
|---|---|---|---|---|
| 5,291,572 A | * | 3/1994 | Blonder | G02B 6/4202 257/E23.193 |
| 2012/0276856 A1 | * | 11/2012 | Joshi | A61N 1/37229 455/73 |
| 2017/0224856 A1 | * | 8/2017 | Mazzeo | A61L 2/14 |

* cited by examiner

*Primary Examiner* — Lindsey G Wehrheim

(57) ABSTRACT

The present disclosure provides medical devices and methods of manufacturing medical devices wherein the medical device includes at least one bonding surface that has been roughed by laser etching to increase its surface area and improve its bonding characteristics. In many embodiments, the medical device is an implantable medical device that includes a hermetically sealed metallic housing that is bonded to a prefabricated non-metallic header. The hermetically sealed metallic housing includes at least one surface that has been subjected to a laser etching and roughening process to increase its surface area and improve its bonding characteristics. The laser etched surface may include spots created in a non-overlapping honeycomb-type pattern that may additionally include a series of spikes protruding therefrom to further improve bonding characteristics.

12 Claims, 6 Drawing Sheets

IMPLANTABLE MEDICAL DEVICES INCLUDING A LASER ETCHED SURFACE IN BONDED AREAS

FIELD OF THE DISCLOSURE

The present disclosure relates generally to medical devices and to methods for assembling medical devices having improved bonding. More particularly, the present disclosure relates to implantable medical devices, and methods of assembling implantable medical devices, that include at least one laser etched bonding surface to increase the surface area thereof and to improve the bonding properties of the laser etched surface. The present disclosure is applicable to a variety of implantable medical devices of the type having a pre-fabricated polymeric part to be coupled to a metallic housing part, such as an implantable cardioverter defibrillator.

BACKGROUND

Many implantable medical devices, such as cardiac pacemakers and the like, are generally designed to be implanted in a "pocket" of fatty tissue near the patient's upper chest or lower abdomen. Accordingly, electronic circuits within the device are hermetically sealed within a housing made of a material that is compatible with body tissue, such as titanium or stainless steel. Electrical connection from the outside with the electronic circuits within the hermetically sealed housing is accomplished via a connector assembly, often referred to as a header or header assembly that is mounted on the housing. The header is generally constructed of a polymeric material, such as a polyurethane or the like. Feedthrough terminals that pass through the hermetically sealed housing are connected with the pacemaker electronic circuits in the housing and with a lead pin receptacle in the connector assembly. At a proximal end, a lead conductor is provided with a lead pin for being received in the connector receptacle and at a distal end, the lead conductor is provided with electrodes for electrical tissue stimulation at the desired tissue location.

In order to ensure good electrical contact between the circuits with the housing and the outside, and to provide sufficient strength of the implantable device, it is desirable to achieve a strong and reliable joint or bond between the polymeric header and the metallic housing. Generally, the header is connected to the housing by either injecting a thermosetting polymer (such as an epoxy, for example) into the header-housing interface through a backfill process or the header-housing is injection molded. This creates the desired attachment and electrical sealing. In either case, the polymer utilized must bond to the housing in order to attach the header properly. In many cases, an anchor is also welded to the housing and used to further strengthen the bond.

Generally, in order for the polymer to effectively bond with the housing, the bonding surface on the housing is roughened to increase the surface area that is subsequently bonded to thereby decrease the shear stress on the interface created between the housing and header. Surface roughening has conventionally been accomplished using a grit blasting process wherein the bonding surface is blasted with silicone particles using compressed air. The silicone particles become embedded in the surface and create a textured surface to which the polymer bonds. Although conventional grit blasting processes suitably increase the surface area of the treated surface to improve the resulting bond, it would be desirable to provide alternative improved processes for increasing the surface area of the bonding surface and improving the resulting bonds between a metallic housing and a polymeric header.

BRIEF SUMMARY OF THE DISCLOSURE

The present disclosure provides medical devices that include one or more bonding surfaces that have been laser etched to roughen the surface and increase its surface area to improve and promote the adhesion and bonding of dissimilar materials. In many embodiments, the medical device is an implantable medical device that includes at least a hermetically sealed housing and a prefabricated header wherein the hermetically sealed housing is constructed of a metallic material and the prefabricated header is constructed of a polymeric, non-metallic material. The metallic material includes at least one bonding surface that has been laser etched or roughened to increase its surface area through roughening and to improve its bonding characteristics, in some embodiments, the laser etched or roughened surface will include a series of spots thereon that may be arranged in a non-overlapping honeycomb or similar type pattern wherein the spots are tangent to one another and may include multiple spikes protruding therefrom to increase bonding strength. In other embodiments, the present disclosure provides methods of manufacturing an implantable medical device including a step of laser etching at least a portion of one bonding surface to improve its bonding characteristics as described herein. Various alternative embodiments of the present disclosure are set forth herein.

In one embodiment, the present disclosure is directed to an implantable medical device. The implantable medical device comprises: (i) a hermetically sealed housing including a laser etched first bonding surface and enclosing electronic circuitry, wherein the laser etched first bonding surface comprises spots arranged in a honeycomb pattern; and (ii) a pre-fabricated header including a second bonding surface, the pre-fabricated header configured for receiving conducting leads and comprising electrically conductive elements that electrically connect the conducting leads to the electronic circuitry of the housing.

In another embodiment, the present disclosure is directed to an implantable medical device comprising: (i) a first component constructed from a metallic material and having a first laser etched bonding surface, wherein the laser etched first bonding surface comprises spots arranged in a honeycomb pattern, wherein the spots have an average depth of from about 0.210 mil to about 0.700 mil, and wherein the spots are tangent to one another and include multiple spikes protruding therefrom; and (ii) a second component constructed from a medical grade polymer material and having a second bonding surface. The first bonding surface and the second bonding surface form a bonding interface.

In another embodiment, the present disclosure is directed to a method of manufacturing an implantable medical device. The method comprises: (i) laser etching a first bonding surface of a hermetically sealed metallic housing enclosing electronic circuitry to roughen and increase the surface area of the first bonding surface by creating spots arranged in a honeycomb pattern on the first bonding surface, wherein the spots are tangent to one another and include multiple spikes protruding therefrom; and (ii) bonding the first bonding surface to a second bonding surface of a pre-fabricated non-metallic header configured for receiving conducting leads and comprising electrically conductive elements that electrically connect the conducting leads to the electronic circuitry of the housing.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessary to scale.

DETAILED DESCRIPTION OF THE DISCLOSURE

Figure 1:
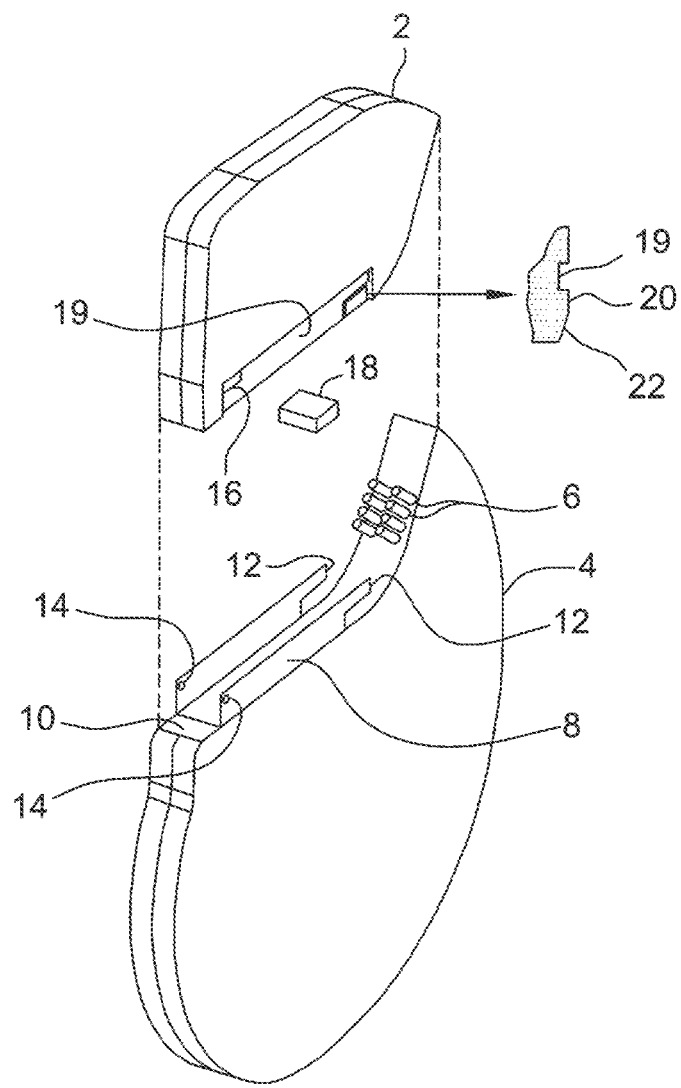
FIG. 1 is an exploded view of a conventional implantable medical device.

The present disclosure provides medical devices and methods of manufacturing medical devices wherein the medical device includes at least one metallic bonding surface that has been roughened by laser etching to increase its surface area and improve its bonding characteristics when bonded to a similar or dissimilar material. In many embodiments, the medical device is an implantable medical device that includes a hermetically sealed metallic housing that is bonded to a non-metallic prefabricated header. The hermetically sealed metallic housing includes at least one surface that has been subjected to a laser etching and roughening process to increase its surface area and improve its bonding characteristics when bonded to a material having a different coefficient of thermal expansion.

More specifically, the present disclosure provides an advantageous alternative surface roughening process for metallic bonding surfaces present on medical devices. This alternative process utilizes laser etching to roughen (that is, increase the overall surface roughness) the bonding surface prior to bonding with a thermosetting polymer or the like (an epoxy, for example) to create small pockets for the bonding agent to flow into, thus creating additional mechanical locking that is important to increasing the strength between the two parts being bonded. The disclosed laser etching/roughening process is a highly consistent, repeatable automatic process that can produce precise, controlled roughened surfaces consistently and quickly. Because the disclosed laser processes disclosed herein are extremely precise such that only the predetermined bonding surface is altered, none of the wires, connectors, or feedthroughs present on many medical devices, such as implantable medical devices, need to be protected or covered during the laser etching process. The laser processes are extremely clean as no foreign material is introduced onto the bonding surface and the laser melts only the top layer of metal (such as titanium, for example) into a textured surface so there is not any material embedded into to the metal. The laser process also cleans the treated surface as the etching is accomplished. As such, there is no need for washing of the metallic surface after laser treatment to remove unwanted material therefrom. Additionally, the laser etching processes described herein eliminate the potential of material breaking away from the bonding surface (as no material is embedded therein) and are also highly adjustable to create different patterns and depths of surface roughening to provide varying bonding properties as desired.

In many embodiments described herein, the disclosed laser etching processes eliminate the need for the welding procedure commonly used to attach a metallic anchor to the housing of an implantable medical device during manufacturing to facilitate the joining of the prefabricated header thereto. The metallic anchor may be eliminated in many embodiments from the implantable medical device as the laser etched and roughened surface provides for a resulting bond between the housing and the prefabricated header that is sufficiently strong to meet strength and load requirements. This results in a time, material, and cost savings.

Although described primarily herein with respect to an implantable medical device, it will be recognized by one skilled in the art based the disclosure that the present laser etching and roughening processes and manufacturing processes disclosed are applicable to a wide range of medical device wherein a metallic surface is bonded to another metallic or non-metallic surface. The metallic bonding surface may be suitably treated with the laser etching process described herein and prepared for bonding to another metallic surface, a plastic, or thermoplastic surface, or another type of surface.

Referring now to the Figures, FIG. 1 illustrates a conventional implantable medical device. The conventional implantable medical device includes a prefabricated header 2 that may be constructed of a polymeric material, including for example a medical grade polymer such as polyurethane. The implantable medical device further includes a hermetically sealed housing 4 that may be constructed of a metallic material, including for example titanium or stainless steel. Hermetically sealed housing 4 includes feedthrough terminals 6 that are electrically connected to electronic circuits (not shown) inside of hermetically sealed housing 4. Prefabricated header 2 further includes a connector receptacle for receiving a connector pin at the proximal end of a pacing lead (not shown).

A housing fastener part formed of a metallic material and in the form of a U-shaped bracket 8 is attached to the hermetically sealed housing 4 by welding. U-shaped bracket 8 is attached to a surface 10 of hermetically sealed housing 4, which faces prefabricated header 2 when prefabricated header 2 and hermetically sealed housing 4 are joined together. U-shaped bracket 8 extends along a major portion of surface 10. The two sides of U-shaped bracket 8 protrude from hermetically sealed housing 4 and extend towards prefabricated header 2 in a direction that is perpendicular to surface 10.

At one end of U-shaped bracket 8, each side of U-shaped bracket 8 is provided with an undercut leaving a finger portion 12. At the other end of U-shaped bracket 8, each side of U-shaped bracket 8 is provided with a through hole 14.

Prefabricated header 2 is provided with a through going hole 16. A header fastener part in form of a metal element 18 is inserted in through going hole 16. Metal element 18 is exposed at each side of prefabricated header 2 at each end of through going hole 16.

The thickness of prefabricated header 2 at the end facing hermetically sealed housing 4 when prefabricated header 2 is mounted to hermetically sealed housing 4, is slightly less than the distance between the two sides of U-shaped bracket 8, so that prefabricated header 2 will fit between the two sides of shaped bracket 8. This reduced thickness portion 19 of prefabricated header 2 is made slightly larger than the size of the U-shaped bracket 8 to avoid tolerance problems. At one end of reduced thickness portion 19, a hook portion 20 with full thickness extends into reduced thickness portion 19. Between hook portion 20 and reduced thickness portion 19, prefabricated header 2 is provided with a beveled portion 22.

Figure 2:
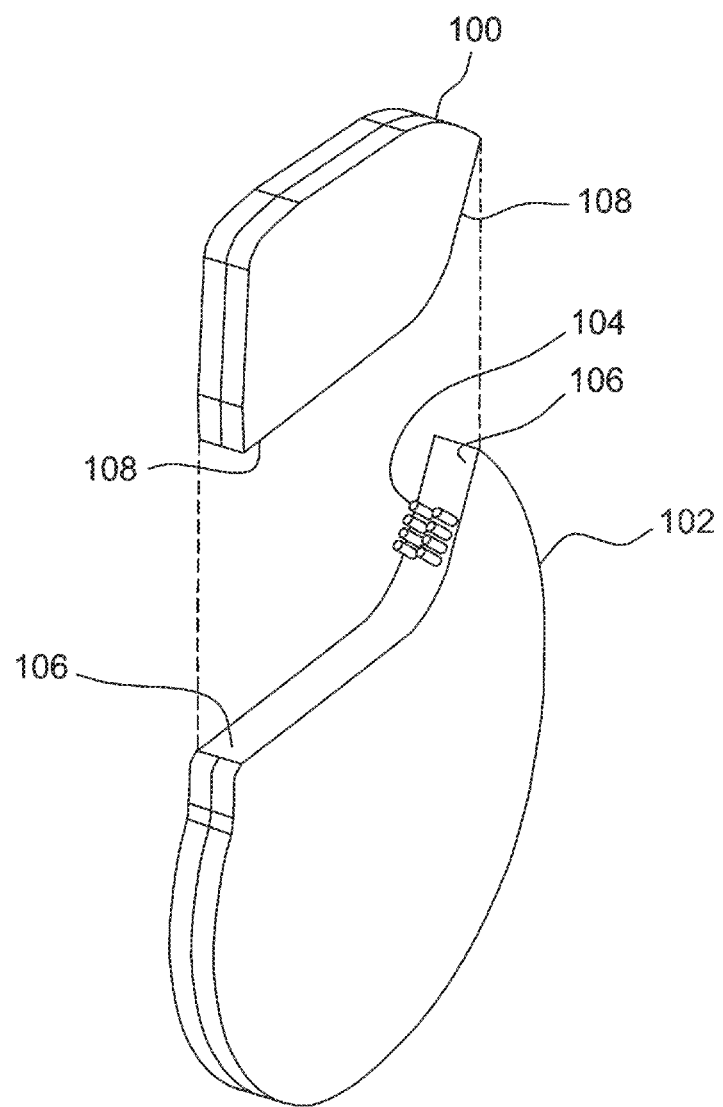
FIG. 2 is an exploded view of an implantable medical device according to one embodiment of the present disclosure.

Referring now to FIG. 2, an implantable medical device according to one embodiment of the present disclosure is shown. The implantable medical device includes prefabricated header 100 and a hermetically sealed housing 102. Hermetically sealed housing 102 includes feedthrough terminals 104 that are electrically connected to electronic circuits (not shown) inside of hermetically sealed housing 102. Prefabricated header 100 further includes a connector receptacle for receiving a connector pin at the proximal end of a pacing lead (not shown). Hermetically sealed housing 102 includes bonding surface 106 that comes into contact with bonding surface 108 of prefabricated header 100 during manufacture. Bonding surface 106 of hermetically sealed housing 102 may be subjected to a laser etching/roughening procedure in accordance with the present disclosure to increase the surface area thereof to improve its bonding characteristics. Bonding surface 108 of prefabricated header 100 is generally not suitable for the laser etching/roughening procedure as prefabricated header 100 is not constructed of a metallic material. When bonding surface 106 and bonding surface 108 are brought together during manufacturing, a suitable bonding agent (not shown), such as a thermosetting polymer (e.g., epoxy) or the like is utilized to facilitate the attachment and provide for electrical sealing.

Figure 3:
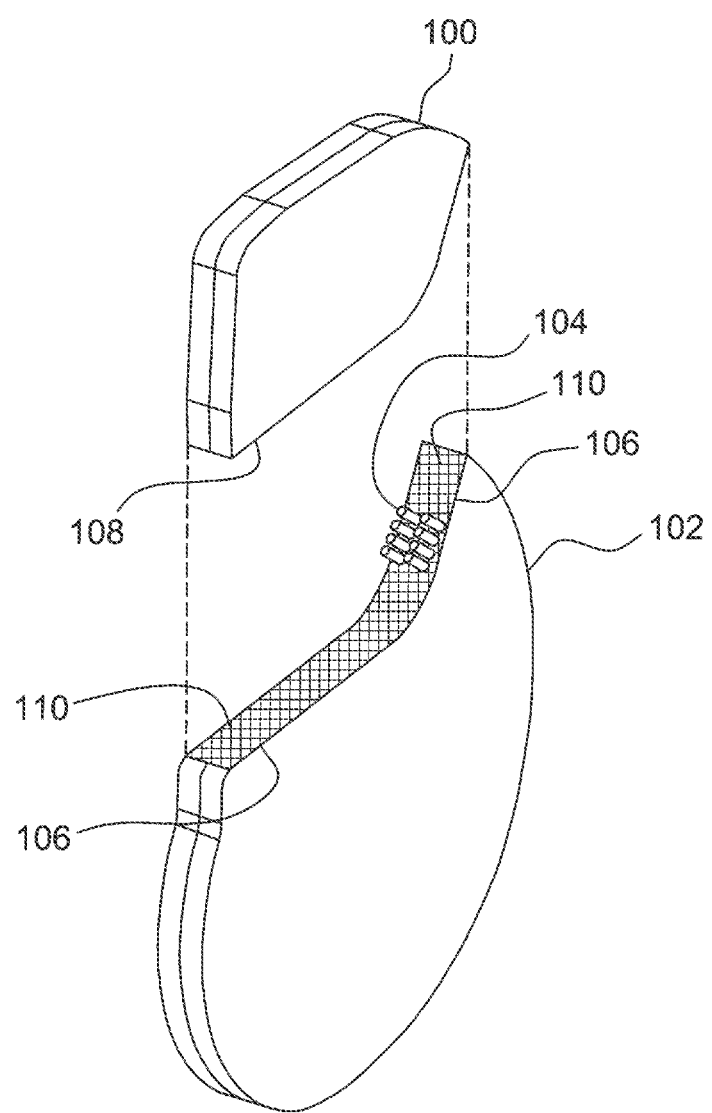
FIG. 3 is an exploded view of the implantable medical device of FIG. 2 further including a laser etched surface on one bonding surface.

Referring now to FIG. 3, there is shown the implantable medical device of FIG. 2 having prefabricated header 100, hermetically sealed housing 102, feedthrough terminals 104, bonding surface 108 and further including a laser etched surface 110 on hermetically sealed housing 102. Although illustrated in FIG. 3 as covering the entirety of bonding surface 106, it is within the scope of the present disclosure for the laser etching to cover only a portion or portions of bonding surface 106 of hermetically sealed housing 102 such that at least some part of bonding surface 106 remains untreated by laser etching.

In order to increase the surface area of bonding surface 106, bonding surface 106 is exposed to pulses of laser irradiation to create a roughened surface having increased surface area to improve bonding characteristics of the surface. Any suitable laser may be used as the source of laser irradiation to roughen the desired surface prior to bonding. In many embodiments, a fiber laser is desirable to create the desired roughened surface. Generally, all or portions of bonding surface 106 is laser etched to create an average surface roughness ($R_a$) of from about 0.5 micrometers to about 10 micrometers, including from about 1 micrometer to about 5 micrometers, and further including from about 2 micrometers to about 3 micrometers. In many embodiments, the limiting feature for the amount of surface roughening that can be safely done and consistently repeated will be the thickness of the hermetically sealed housing; that is, the amount of roughening accomplished on all or portions of bonding surface 106 should generally not compromise the integrity or strength of the hermetically sealed housing by etching too deeply therein. In many embodiments, the desired surface roughness will be created using a crosshatch pattern to etch a series of grooves into the desired metallic surface wherein each groove may have a width of up to about 3 mil and a depth of at least 0.5 mil, or even 1.0 mil, or even 1.5 mil. Other groove widths and groove depths and patters are also within the scope of the present disclosure and may also provide the numerous benefits detailed herein.

The pulses of laser irradiation exposed to the bonding surface create spots on the surface thereof to increase the bonding surface area. Additionally, in many embodiments as described herein, the pulses of laser irradiation exposed to the bonding surface create a series of spikes protruding from the surface to further improve the resulting bonding characteristics as further described herein. In many embodiments, it is desirable for the spots created on the bonding surface to not overlap one another so that the surface area created is maximized to improve bonding characteristics. In some embodiments, the spots created on the laser irradiated surface may be created in a honeycomb or similar pattern wherein the spots are tangent (non-overlapping) to one another to maximize surface area, as further described below and illustrated in FIG. 6. When a non-overlapping honeycomb spot pattern is created by the laser spots on the bonding surface, the bond resulting therefrom is highly resistant to shear stress and delamination which can occur due to the differences in thermal expansion between metallic and non-metallic materials. In many embodiments of the present disclosure, a laser beam that produces a spot size of from about 25,000 to about 250,000 nanometers is utilized to create a spot diameter on the surface of from about 25 micrometers to about 250 micrometers. In some embodiments, the number of pulses of laser irradiation per spot ranges from about 10 to about 500 pulses, desirably from about 50 to about 400 pulses, and desirably from about 100 to about 300 pulses.

A number of parameters of the laser etching process impact and determine the resulting characteristics of the laser etched surface. These parameters include, for example, the number of passes the laser makes over the desired bonding area surface, the power setting of the laser, the frequency of the laser, and the mark speed at which the laser moves over the bonding surface. Each parameter should be considered in relation to one another to balance the speed of the laser etching process, the quality of the resulting laser etching, the depth of the etching created, the pattern of the etching created, and the amount of heat created on the surface during the laser etching process. In many embodiments, it is desirable to keep the temperature created on the surface of the material being etched less than about 60° C., or even less than about 50° C. so as to maintain the integrity of many electrical components contained with the hermetically sealed housing.

The number of passes the laser makes over the desired bonding area may generally range from about 1 to about 10, including from about 1 to about 5, including from 1 to 2. The power of the laser may range from about 70% to about 90% and the frequency may range from about 5 to about 500 kHz. The mark speed may generally range from about 5 inches/second to about 200 inches/second. In one desirable embodiment, number of passes is about 2, the laser power is about 70-90%, the laser frequency is about 35-50 kHz, the mark speed is about 50-150 inches/second and the fill mode is bi-directional. One suitable laser for performing the laser etching of the bonding surface of the present disclosure is an LMF-2000-SM Fiber Laser Marker (Amada Miyachi America, Inc., Monrovia, Calif.).

Figure 5:
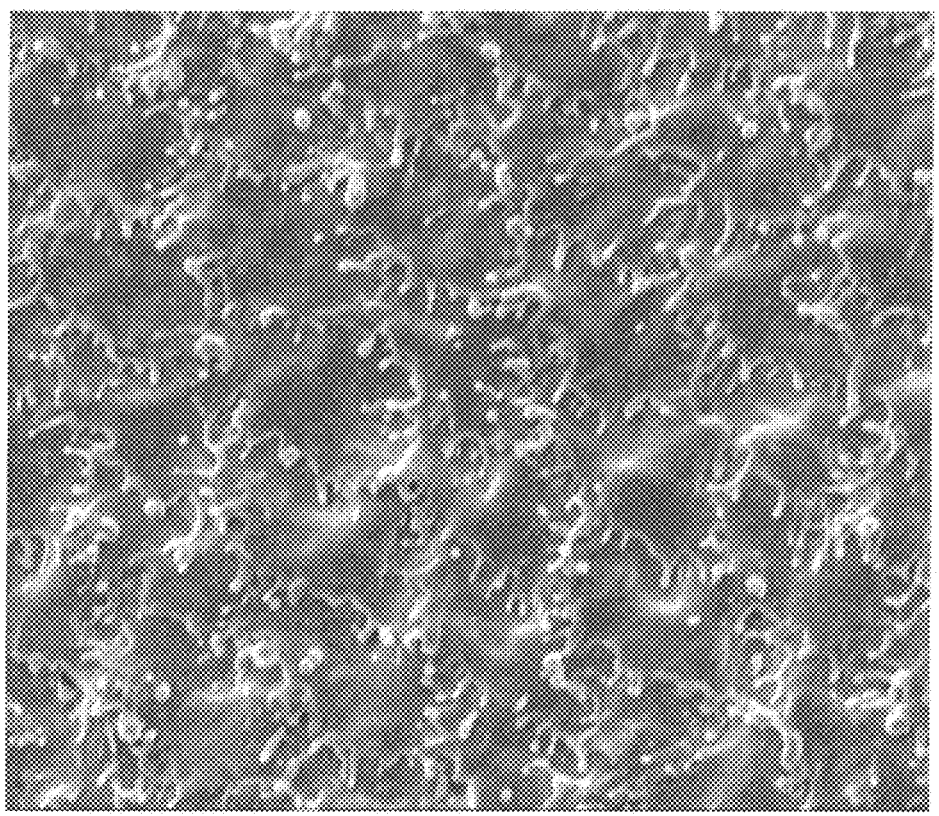
FIG. 5 is a photograph of a laser etched titanium surface of the present disclosure at 1000 times magnification.

Referring now to FIG. 5, there is shown a 1000 times magnification of a laser etched surface of titanium in accordance with the present disclosure. As shown in FIG. 5, laser etching of the surface creates a highly consistent patterned surface including spikes protruding from the surface that does not introduce foreign material (in contrast to grit blasting discussed above that introduces silicone particles onto the surface) onto the surface that could potentially break off of the surface at a later time causing potential contamination. The patterned surface is also highly reproducible such that medical devices produced therefrom are highly consistent in performance and reliability.

As noted herein, in some desirable embodiments of the present disclosure, the spots created on the bonding surface to increase the resulting surface area for bonding may be created in a non-overlapping honeycomb pattern wherein the spots are tangent to one another to maximize surface area. These created spots on the bonding surface may generally have a depth of from about 0.210 mil to about 0.700 mil, or even from about 0.216 mil to about 0.690 mil to increase surface area and further the desired bonding characteristics. The depth of the spots created on the surface may be controlled by the number of passes and the percent of laser powered applied to the surface on each pass and should not penetrate too deeply into the surface so as to cause any type of structural integrity issue or damage to internal electrical or other components. In many of these embodiments, the spots include a series of spikes protruding therefrom to further improve the resulting bonding characteristics of the treated surface. The series of formed spikes on the surface are created when splashed molten material resulting from the laser process cools on the treated surface. Subsequently during the device manufacturing process when epoxy (or another similar bonding material) is introduced onto the laser treated surface, the formed spikes will interact therewith and act as an anchoring mechanism to reinforce the epoxy at the bonding interface and increase the resulting formed joint strength.

Figure 6:
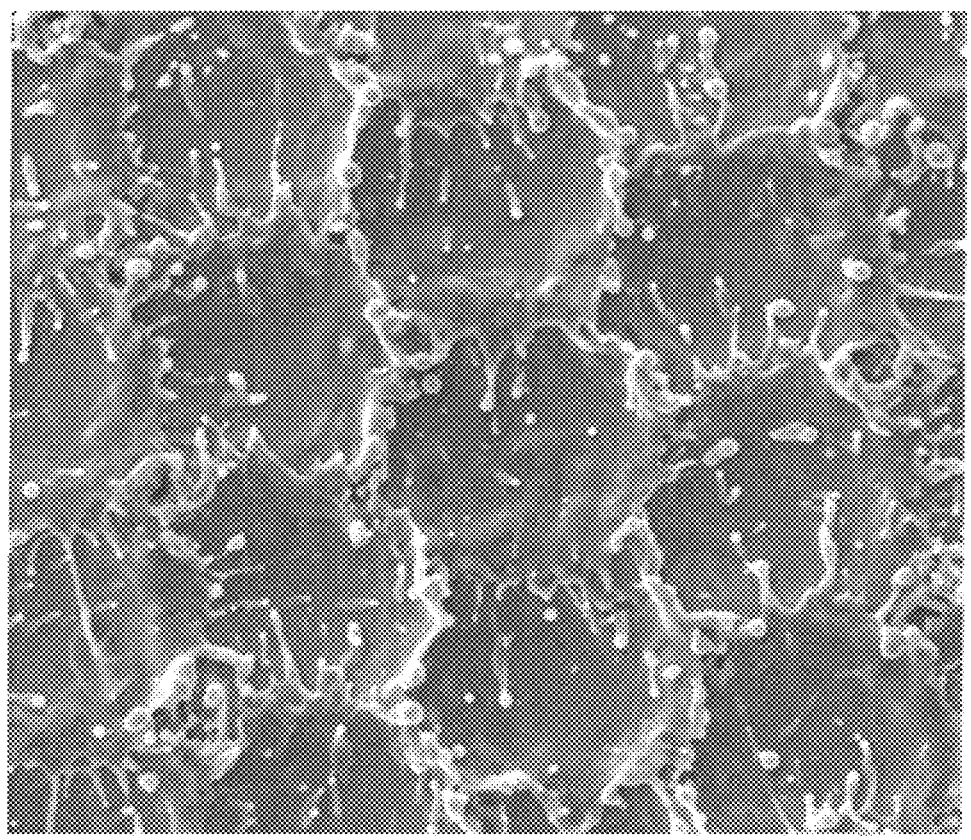
FIG. 6 is a photograph of a laser etched titanium surface of the present disclosure at 500 times magnification.

Referring now to FIG. 6, there is shown a 500 times magnification of one embodiment of a laser etched surface of the present disclosure. As shown, the laser etched surface is etched in the form of non-overlapping spots in a honeycomb pattern wherein the spots are tangent to one another and the resulting surface area maximized. FIG. 6 further shows numerous spikes protruding from the etched spots, which act to further improve bonding as described herein.

Figure 4:
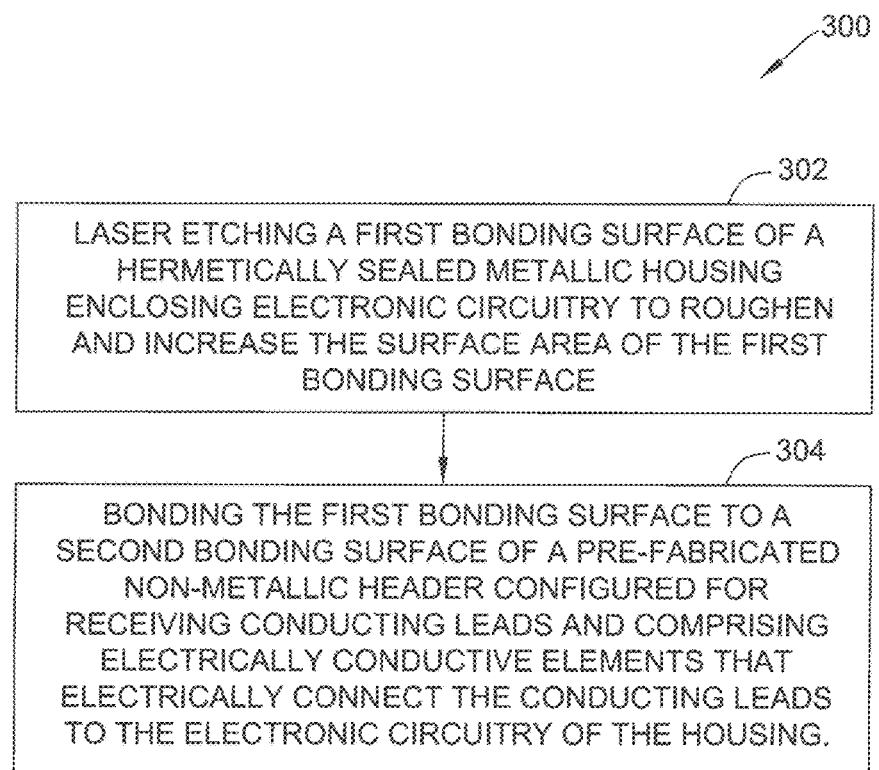
FIG. 4 is a flow chart illustration one method of manufacturing an implantable medical device of the present disclosure.

In accordance with the present disclosure, there are also provided methods of manufacturing medical devices, including implantable medical devices, incorporating the laser etching/roughening processes as described herein. The implantable medical devices may include, for example, implantable cardioverter defibrillators, implantable cardiac pacemakers, insertable cardiac monitors, implantable nerve stimulators, and other implantable active medical devices. In one specific embodiment, a method of manufacturing an implantable medical device comprises: (i) laser etching a first bonding surface of a hermetically sealed metallic housing enclosing electronic circuitry to roughen and increase the surface area of the first bonding surface; and (ii) bonding the first bonding surface to a second bonding surface of a pre-fabricated non-metallic header configured for receiving conducting leads and comprising electrically conductive elements that electrically connect the conducting leads to the electronic circuitry of the housing. FIG. 4 is a flow chart of one embodiment of a method 300 of manufacturing an implantable medical device. Method 300 includes laser etching 302 a first bonding surface of a hermetically sealed metallic housing enclosing electronic circuitry to roughen and increase the surface area of the first bonding surface; and bonding 304 the first bonding surface to a second bonding surface of a pre-fabricated non-metallic header configured for receiving conducting leads and comprising electrically conductive elements that electrically connect the conducting leads to the electronic circuitry of the housing.

Example 1

In this Example, thirteen housings constructed of titanium were subjected to a laser etching process using a fiber laser to create surface roughening on a bonding surface prior to epoxy bonding of that treated surface with a prefabricated header constructed of a polyurethane to form an implantable medical device for further testing in Example 2. The bonding surface of the titanium housing was subjected to a laser etching process wherein a crosshatch pattern was used to etch a series of grooves into the surface of the titanium material to increase the surface area thereof as described herein. The laser utilized for the etching process was an LMF-2000-SM Fiber Laser Marker (Amada Miyachi America, Inc, Monrovia, Calif.) including a 160 mm f-Theta Lens and a 6× Beam Expander. The grooves created in the bonding surface of the titanium housing did not exceed about 3 mil in width and were at least 1.0 mil to 1.5 mil in depth. The laser was set at 90% Power, a speed of 105 inches/second, and a frequency of 35 kHz. A total of two passes was completed on each titanium housing surface treated to provide a resulting $R_a$ of about 1.8-2.2 micrometers on the treated surface of the titanium housing.

Example 2

In this Example, 13 implantable medical devices including a laser etched titanium housing and a prefabricated polyurethane header from Example 1 were fabricated and tested to determine the mechanical bonding properties and capabilities between the housing and the header using lateral loading against the side of the header. This test directly reflects the performance of the bonding surface. The titanium housing should be securely attached (bonded) to the polyurethane header to withstand any static or cyclic bad applied before or after implantation to prevent separation of one from the other. Separation or delamination between the titanium housing and the polyurethane header may create a path for body fluids to penetrate and negatively impact feedthrough wires.

An Instron Force Tester 3342 (Instron, Norwood, Mass.) was utilized to carry out the push testing of the samples to determine lateral loading capabilities of the 13 test samples. The push bad was applied to the septum location farthest from the header to housing interface. The maximum bad (lbf) of each test sample ranged from about 82 to about 107, which far exceeded the minimum requirement of 12 lbf. This indicates that the laser etching process provides for a consistent maximum bad and high strength bond between the housing and header.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like)

are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable medical device comprising:
    a first component constructed from a metallic material and having a laser etched first bonding surface; and
    a second component constructed from a medical grade polymer material and having a second bonding surface;
    wherein the first bonding surface and the second bonding surface form a bonding interface.

2. The implantable medical device of claim 1, further comprising:
    a thermosetting polymer positioned at the bonding interface.

3. The implantable medical device of claim 1, wherein the laser etched first bonding surface has an $R_a$ of from about 0.5 micrometers to about 10 micrometers.

4. The implantable medical device of claim 1, wherein the laser etched first bonding surface has an $R_a$ of from about 2 micrometers to about 3 micrometers.

5. The implantable medical device of claim 1, wherein the laser etched first bonding surface has a crosshatch pattern.

6. The implantable medical device of claim 1, wherein the first component is constructed from a metallic material selected from the group consisting of titanium and stainless steel.

7. The implantable medical device of claim 1, wherein the second component is constructed of a medical grade polyurethane.

8. A method of manufacturing an implantable medical device, the method comprising:
    laser etching a first bonding surface of a hermetically sealed metallic housing enclosing electronic circuitry to roughen and increase the surface area of the first bonding surface; and
    bonding the first bonding surface to a second bonding surface of a pre-fabricated non-metallic header configured for receiving conducting leads and comprising electrically conductive elements that electrically connect the conducting leads to the electronic circuitry of the housing.

9. The method of claim 8, wherein the first bonding surface has an $R_a$ of from about 0.5 micrometer to about 10 micrometers.

10. The method of claim 8, wherein the first bonding surface has an $R_a$ of from about 2 micrometers to about 3 micrometers.

11. The method of claim 8, wherein the bonding includes using a thermosetting polymer.

12. The method of claim 8, wherein the first bonding surface has been roughened using a crosshatch pattern.

* * * * *